(12) United States Patent
Lambrecht et al.

(10) Patent No.: US 11,517,397 B2
(45) Date of Patent: *Dec. 6, 2022

(54) INSTRUMENT FLUSHING SYSTEM

(71) Applicant: Intuitive Surgical Operations, Inc., Sunnyvale, CA (US)

(72) Inventors: Bram Gilbert Antoon Lambrecht, Sunnyvale, CA (US); S. Christopher Anderson, Sunnyvale, CA (US); Thomas G. Cooper, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 32 days.

This patent is subject to a terminal disclaimer.

(21) Appl. No.: 17/306,498

(22) Filed: May 3, 2021

(65) Prior Publication Data
US 2021/0251719 A1   Aug. 19, 2021

Related U.S. Application Data

(63) Continuation of application No. 16/317,222, filed as application No. PCT/US2017/038689 on Jun. 22, 2017.
(Continued)

(51) Int. Cl.
*A61B 90/70* (2016.01)
*B08B 9/032* (2006.01)
(Continued)

(52) U.S. Cl.
CPC .............. *A61B 90/70* (2016.02); *A61B 34/30* (2016.02); *B08B 9/032* (2013.01);
(Continued)

(58) Field of Classification Search
USPC .......................................................... 600/1
See application file for complete search history.

(56) References Cited

U.S. PATENT DOCUMENTS

| 793,510 A | 6/1905 | Cramer et al. |
|---|---|---|
| 4,589,403 A | 5/1986 | Ouchi et al. |

(Continued)

FOREIGN PATENT DOCUMENTS

| CN | 101040775 A | 9/2007 |
|---|---|---|
| CN | 101513338 A | 8/2009 |

(Continued)

OTHER PUBLICATIONS

Extended European Search Report for EP Application No. 17828155.6, dated Feb. 4, 2020.
(Continued)

*Primary Examiner* — John R Downey
*Assistant Examiner* — Anant A Gupta (57) ABSTRACT

A medical instrument includes an instrument shaft with exit holes near a distal end of the shaft, a tool coupled to the distal end of the shaft, and a backend. The backend may include a mechanism that manipulates a drive element that extends through the shaft and couples to the tool, a fluid inlet, and a fluid channel assembly providing fluid communication between the fluid inlet and the proximal end of the shaft. Cleaning fluid is directed into the fluid inlet, through the fluid channel assembly, and into the shaft. A chassis or other structural piece of the backend may form part of the fluid channel assembly.

20 Claims, 5 Drawing Sheets

Related U.S. Application Data (60) Provisional application No. 62/362,386, filed on Jul. 14, 2016.

(51) Int. Cl.
    *A61B 34/30* (2016.01)
    *A61B 17/29* (2006.01)
    *A61B 17/00* (2006.01)

(52) U.S. Cl.
    CPC .............. *A61B 2017/00477* (2013.01); *A61B 2017/2908* (2013.01); *A61B 2034/302* (2016.02); *B08B 2209/032* (2013.01)

(56) References Cited

U.S. PATENT DOCUMENTS

| | | |
|---|---|---|
| 4,860,742 A | 8/1989 | Park et al. |
| 5,108,060 A | 4/1992 | Beele |
| 5,792,135 A | 8/1998 | Madhani et al. |
| 5,876,325 A | 3/1999 | Mizuno et al. |
| 6,331,181 B1 | 12/2001 | Tierney et al. |
| 6,371,952 B1 | 4/2002 | Madhani et al. |
| 6,394,998 B1 | 5/2002 | Wallace et al. |
| 6,817,974 B2 | 11/2004 | Cooper et al. |
| 6,994,708 B2 | 2/2006 | Manzo |
| 7,090,683 B2 | 8/2006 | Brock et al. |
| 7,169,141 B2 | 1/2007 | Brock et al. |
| 7,214,230 B2 | 5/2007 | Brock et al. |
| 7,331,967 B2 | 2/2008 | Lee et al. |
| 7,371,210 B2 | 5/2008 | Brock et al. |
| 7,524,320 B2 | 4/2009 | Tierney et al. |
| 7,666,191 B2 | 2/2010 | Orban, III et al. |
| 7,935,130 B2 | 5/2011 | Williams |
| 8,241,271 B2 | 8/2012 | Millman et al. |
| 8,444,631 B2 | 5/2013 | Yeung et al. |
| 8,479,969 B2 | 7/2013 | Shelton, IV |
| 8,506,555 B2 | 8/2013 | Ruiz Morales |
| 8,551,115 B2 | 10/2013 | Steger et al. |
| 8,771,270 B2 | 7/2014 | Burbank |
| 8,800,838 B2 | 8/2014 | Shelton, IV |
| 9,028,494 B2 | 5/2015 | Shelton, IV et al. |
| 9,078,684 B2 | 7/2015 | Williams |
| 9,192,448 B2 | 11/2015 | Blumenkranz |
| 9,204,923 B2 | 12/2015 | Manzo et al. |
| 9,232,979 B2 | 1/2016 | Parihar et al. |
| 9,259,274 B2 | 2/2016 | Prisco |
| 10,130,366 B2 | 11/2018 | Shelton, IV et al. |
| 10,478,256 B2 | 11/2019 | Shelton, IV et al. |
| 10,595,949 B2 | 3/2020 | Donlon et al. |
| 11,000,345 B2 | 5/2021 | Lambrecht et al. |
| 2002/0000253 A1 | 1/2002 | Fillmore et al. |
| 2002/0111635 A1 | 8/2002 | Jensen et al. |
| 2005/0119527 A1 | 6/2005 | Banik et al. |
| 2005/0234434 A1 | 10/2005 | Sunaoshi |
| 2007/0005002 A1 | 1/2007 | Millman et al. |
| 2007/0043338 A1 | 2/2007 | Moll et al. |
| 2007/0106204 A1 | 5/2007 | Fedenia et al. |
| 2007/0232858 A1 | 10/2007 | MacNamara et al. |
| 2008/0046122 A1 | 2/2008 | Manzo et al. |
| 2008/0065102 A1 | 3/2008 | Cooper |
| 2008/0065105 A1 | 3/2008 | Larkin et al. |
| 2008/0087871 A1 | 4/2008 | Schena et al. |
| 2008/0103491 A1 | 5/2008 | Omori et al. |
| 2008/0196533 A1 | 8/2008 | Bergamasco et al. |
| 2009/0088774 A1 | 4/2009 | Swarup et al. |
| 2009/0198272 A1 | 8/2009 | Kerver et al. |
| 2009/0216248 A1 | 8/2009 | Uenohara et al. |
| 2009/0270899 A1 | 10/2009 | Carusillo et al. |
| 2010/0011900 A1 | 1/2010 | Burbank et al. |
| 2010/0170519 A1 | 7/2010 | Romo et al. |
| 2010/0175701 A1 | 7/2010 | Reis et al. |
| 2010/0318101 A1 | 12/2010 | Choi et al. |
| 2011/0015650 A1 | 1/2011 | Choi et al. |
| 2011/0118754 A1 | 5/2011 | Dachs, II et al. |
| 2011/0277775 A1 | 11/2011 | Holop et al. |
| 2011/0295269 A1 | 12/2011 | Swensgard et al. |
| 2011/0295270 A1 | 12/2011 | Giordano et al. |
| 2012/0010628 A1 | 1/2012 | Cooper et al. |
| 2012/0123441 A1 | 5/2012 | Au et al. |
| 2012/0239060 A1 | 9/2012 | Orban, III et al. |
| 2012/0289974 A1 | 11/2012 | Rogers et al. |
| 2013/0041392 A1 | 2/2013 | Edwards |
| 2014/0005678 A1 | 1/2014 | Shelton, IV et al. |
| 2014/0005708 A1 | 1/2014 | Shelton, IV |
| 2014/0309625 A1 | 10/2014 | Okamoto et al. |
| 2015/0150635 A1 | 6/2015 | Kilroy et al. |
| 2015/0157355 A1 | 6/2015 | Price et al. |
| 2015/0359599 A1 | 12/2015 | Fagan et al. |
| 2015/0374447 A1 | 12/2015 | Blumenkranz et al. |
| 2016/0184034 A1 | 6/2016 | Holop et al. |
| 2016/0184036 A1 | 6/2016 | Solomon et al. |
| 2016/0193012 A1 | 7/2016 | Anderson et al. |
| 2016/0287346 A1 | 10/2016 | Hyodo et al. |
| 2016/0361049 A1 | 12/2016 | Dachs, II et al. |
| 2018/0055583 A1 | 3/2018 | Schuh et al. |
| 2018/0229021 A1 | 8/2018 | Donlon et al. |
| 2018/0243036 A1 | 8/2018 | Donlon et al. |
| 2019/0038282 A1 | 2/2019 | Shelton, IV et al. |
| 2019/0059988 A1 | 2/2019 | Davison et al. |
| 2019/0223960 A1 | 7/2019 | Chaplin et al. |
| 2019/0298323 A1 | 10/2019 | Lambrecht et al. |
| 2019/0307522 A1 | 10/2019 | Lambrecht et al. |
| 2020/0197117 A1 | 6/2020 | Donlon et al. |
| 2021/0322118 A1 | 10/2021 | Donlon et al. |

FOREIGN PATENT DOCUMENTS

| | | | |
|---|---|---|---|
| CN | 101564284 A | 10/2009 | |
| CN | 101801284 A | 8/2010 | |
| CN | 103079483 A | 5/2013 | |
| CN | 103445815 A | 12/2013 | |
| DE | 8415222 U1 | 9/1984 | |
| EP | 2119404 A1 | 11/2009 | |
| EP | 2979614 A1 | 2/2016 | |
| JP | H06114000 A | 4/1994 | |
| JP | H10249777 A | 9/1998 | |
| JP | 2005288590 A | 10/2005 | |
| JP | 2016097305 A | 5/2016 | |
| WO | WO-9729690 A1 | 8/1997 | |
| WO | WO-2012068156 A2 | 5/2012 | |
| WO | WO-2015023772 A1 * | 2/2015 | ............ A61B 34/30 |
| WO | WO-2015142290 A1 | 9/2015 | |
| WO | WO-2016045041 A1 | 3/2016 | |
| WO | WO-2016161449 A1 | 10/2016 | |
| WO | WO-2016172299 A1 | 10/2016 | |
| WO | WO-2018013313 A1 | 1/2018 | |

OTHER PUBLICATIONS

International Search Report and Written Opinion for Application No. PCT/US2017/038689, dated Oct. 19, 2017, 10 pages.

Non Final Office Action dated Aug. 6, 2020 for U.S. Appl. No. 16/317,222, filed Jan. 11, 2019, 11 pages.

Office Action dated Mar. 3, 2021 for CN Application No. 201780041782.5 filed Jun. 22, 2017, 10 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Notice of Allowance for CN Application No. 2017800417825, dated Aug. 16, 2021, 3 pages.

* cited by examiner

INSTRUMENT FLUSHING SYSTEM

RELATED APPLICATION

This patent application is a continuation of U.S. patent application Ser. No. 16/317,222 (filed Jan. 11, 2019), entitled "INSTRUMENT FLUSHING SYSTEM," which is a U.S. national stage filing under 35 U.S.C. § 371 of International Application No. PCT/US2017/038689 (filed Jun. 22, 2017), entitled "INSTRUMENT FLUSHING SYSTEM," which claims priority to and the filing date benefit of U.S. Provisional Patent Application No. 62/362,386 (filed Jul. 14, 2016), entitled "INSTRUMENT FLUSHING SYSTEM," each of which is incorporated by reference herein in its entirety.

BACKGROUND

Minimally-invasive medical procedures often employ medical instruments having a tool or end effector or other manipulation element at the distal end of an elongated instrument shaft. During such a procedure, the distal end of such a medical instruments may be inserted through small incisions and/or natural lumens to position the distal tools at a work site in a patient, and a surgeon or other medical personnel may control the tools to perform desired clinical functions. The instrument shafts are generally long and thin and may, for example, be over 50 cm in length and less than 1 cm in diameter. Despite the small diameters of some medical instruments, multiple tendons, push-pull elements, and power or signal lines may extend through the length of the instrument shaft.

Complex medical instruments are typically expensive, and users benefit if medical instruments can be reused for multiple procedures. The medical instruments do, however, directly contact patients and must be sterilize for reuse. Before being sterilized, the instrument generally must be cleaned to remove any fluids, particulates, or other contaminants that may have entered the instrument during a previous procedure. Full disassembly of the medical instrument for such cleaning may be impractical, and so systems and methods are needed for cleaning the inside of an instrument shaft that do not require disassembling the instrument.

One cleaning system for a medical instrument includes a flush tube, e.g., a thin walled, flexible, plastic tube that runs the length of the shaft of the medical instrument. The flush tube may particularly extend from a backend (proximal end) of the instrument to a distal end where a tool attaches to the shaft. (In these medical instruments, the ends of structures closest to a robot or other control device are commonly referred to as the "proximal" ends, while the ends closest to the tool are commonly referred to as the "distal" ends.) The proximal end of the flush tube may be connected so that cleaning fluid (e.g., water) may be fed through the flush tube to the distal end of the instrument shaft where the cleaning fluid exits the flush tube. The cleaning fluid from the flush tube hits a seal at the distal end of the instrument shaft and returns back through the instrument shaft, and the returning fluid may flush any contaminants through the inside of the shaft until the cleaning fluid washes contaminants out of the medical instrument through gaps in a backend housing of the medical instrument. For this system, the flush tube must be carefully routed to prevent the flush tube from becoming kinked, because a kink would block the flow of cleaning fluid. Also, the instrument shaft needs to have sufficient internal space for the flush tube, for fluid return, and for any drive cables, drive rods, and electrically energized lines needed for the clinical function of the medical instrument. A medical instrument that provides a high degree of functionality through a small diameter instrument shaft, e.g., an instrument shaft with a diameter less than about 8 mm and particularly having an instrument shaft with articulated joints, may not have space for a flush tube path that can reliably avoid kinking of the flush tube.

SUMMARY

In accordance with an aspect of the invention, a medical instrument routes cleaning fluid in a proximal-to-distal direction through an instrument shaft without use of a flush tube extending though the instrument shaft. Cleaning fluid may exit the instrument shaft though exit holes located near the distal end of the shaft. Joints, such as wrists, and other mechanism at the distal end of the instrument shaft may be flushed using the proximal-to-distal flow or may be subject to direct cleaning through cleaning vents in the distal mechanisms.

One specific implementation of a medical instrument includes a shaft with exit holes near a distal end of the shaft, a tool coupled to the distal end of the shaft, and the backend including: a mechanism that manipulates a drive element that extends through the shaft and couples to the tool; a fluid inlet; and a fluid channel assembly in communication with the fluid inlet and containing the proximal end of the shaft.

Another specific embodiment is a method for cleaning a medical instrument. The method may include allowing the injection of a cleaning fluid into a fluid channel assembly, the fluid channel assembly containing a proximal end of a shaft of the medical instrument. A drive element extends through the fluid channel assembly and through the shaft. The drive element couples to a tool at a distal end of the shaft. The method further includes removing contaminants from inside the shaft by allowing or guiding the cleaning fluid to flow through the shaft in a proximal-to-distal direction. The method further includes facilitating the draining of the cleaning fluid out of the shaft through to exit holes near the distal end of the shaft.

BRIEF DESCRIPTION OF THE DRAWINGS

The drawings illustrate examples for the purpose of explanation and are not of the invention itself. Use of the same reference symbols in different figures indicates similar or identical items.

DETAILED DESCRIPTION

A system and method for cleaning a minimally invasive medical instrument directs a cleaning fluid into a proximal end of an instrument shaft so that the cleaning fluid flows through the instrument shaft in a proximal-to-distal direction and exits the instrument shaft through one or more exit holes at the distal end of the instrument shaft. A cap system at the proximal end of the instrument shaft may provide a close fit (contact or near contact, although not necessarily sealing contact) to drive cables or rods so that a sufficient amount of cleaning fluid fed into a flush channel in the instrument chassis flows into the instrument shaft. The exit holes may be located near the distal end of the solid portion of the instrument shaft. To maintain insufflation pressure during use of the medical instrument, to minimize contamination entering the instrument shaft, and to provide the medical instrument with bending stiffness, strength, and lower cost, the exit holes may be small and only provided near the distal end of the instrument shaft, while the proximal portion of the instrument shaft does not have holes that might otherwise weaken the instrument shaft. A sheath, which may be disposable, may be used to cover the holes during a medical procedure to further minimize insufflation loss and soiling. For convenience, an input cleaning port may be located in the instrument housing of a backend of the medical instrument. A proximal portion of the cleaning system may particularly include a housing or chassis in which the instrument shaft is mounted and which contains a channel or fluid conduit that directs fluid from an external inlet to the proximal end of the instrument shaft. A flush cap through which drive elements and electrical lines may extend into the instrument shaft may cap a fluid trough in the chassis or housing and may provide a close fit to actuation elements such as drive cables or rods.

Although the above examples and other discussions herein often refer to medical procedures and medical instruments, the techniques disclosed also apply to non-medical procedures and non-medical instruments.

Figure 1A:
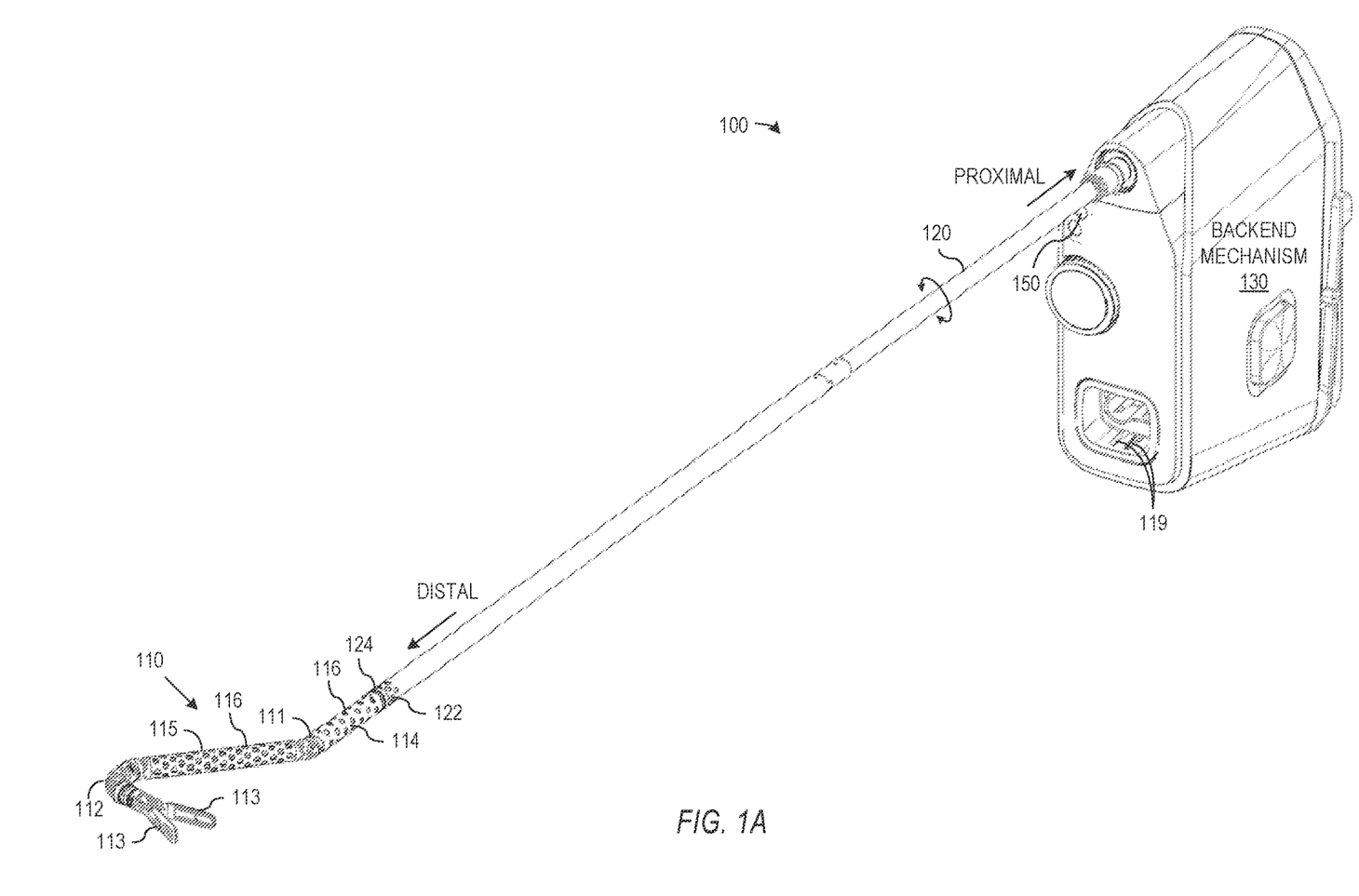
FIGS. 1A and 1B respectively show perspective and top views of an example implementation of a medical instrument using proximal-to-distal flushing.

FIG. 1A shows a perspective view of an example implementation of a medical instrument 100 in accordance with an example implementation using a proximal-to-distal flush. Medical instrument 100 generally includes an end effector (also called a "tool") 110 at a distal end of an elongated instrument shaft 120 that extends from a backend 130. Distal tool 110 and instrument shaft 120 may have multiple degrees of freedom of movement relative to backend 130, and in the illustrated configuration of FIG. 1A, medical instrument 100 has six degrees of freedom corresponding to: two types of actuation of a first wrist or joint 111; two more types of actuation of a second wrist or joint 112; opening or closing movement of jaws 113; and rotations of instrument shaft 120 about its central or length axis. Other implementations of medical instruments may provide more, fewer, or different degrees of freedom of movement.

Figure 1B:
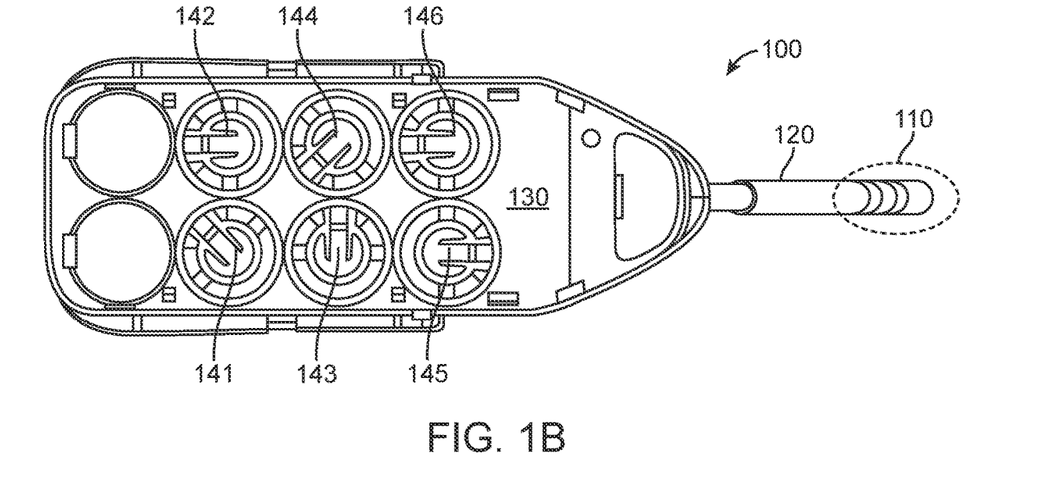

FIG. 1B shows a top view of instrument 100 and particularly illustrates an interface through which instrument 100 may engage and mount on a robotic system. In particular, as shown in FIG. 1B, backend 130 includes six input spindles 141 to 146 with external engagement features that may be shaped and positioned to engage actuators in a docking port of a robotic system such as the da Vinci® Surgical System commercialized by Intuitive Surgical, Inc. During a medical procedure, input spindles 141 and 142 may engage first and second actuators, e.g., drive motors, in the robot, so that the robot can rotate input spindles 141 and 142 to pull drive cables extending to joint 111 and thereby control actuation of wrist or joint 111. Third and fourth actuators in the robot may rotate input spindles 143 and 144 to pull drive cables extending to wrist or joint 112 to thereby control actuation of wrist or joint 112. A fifth actuator may rotate input spindle 145 to push or pull a push-pull rod that extends to jaws 113 and controls opening or closing of jaws 113, and a sixth actuator may rotate input spindle 146 to control roll rotation of instrument shaft 120.

In accordance with one aspect disclosed herein, backend 130 has a flush path that directs cleaning fluid into a proximal end instrument shaft 120 so that fluid flows and flushes around and along the drive elements en route from the proximal end of instrument shaft 120 to exit holes 122 as shown in FIG. 1A. Exit holes 122 in instrument shaft 120 may be near a distal end of a long fluid tight proximal portion of shaft 120. In particular, the proximal fluid tight portion of instrument shaft 120 may be hole-free and therefore may be structurally stronger than if holes where provided along the full length of instrument shaft 120. In distal tool 110, tubular links 114 and 115 may also include holes 116 (also called "vents 116") through which cleaning fluid may be applied to drive elements or other structures in tubular links 114 and 115. The strength of links 114 and 115 may be less critical in some medical systems, since such links are close to the distal end of instrument 100 and therefore support shorter moment arms for external forces. Holes 116 may permit tool 110 to be directly cleaned, e.g., by spraying cleaning fluid from a position adjacent to distal tool 110. In some implementations, a seal 124 may be provided between instrument shaft 120 and tool 110 and may seal around the drive elements that extend through instrument shaft 120 and into distal tool 110. Seal 124 may help maintain insufflation pressure, e.g., prevent distal-to-proximal air flows through holes 116 and back through instrument shaft 120 when gas insufflation inflates a work site for a medical procedure. Seal 124 may also reduce or minimize the entry of blood, particulates, or other contaminants into instrument shaft 120.

Figure 2:
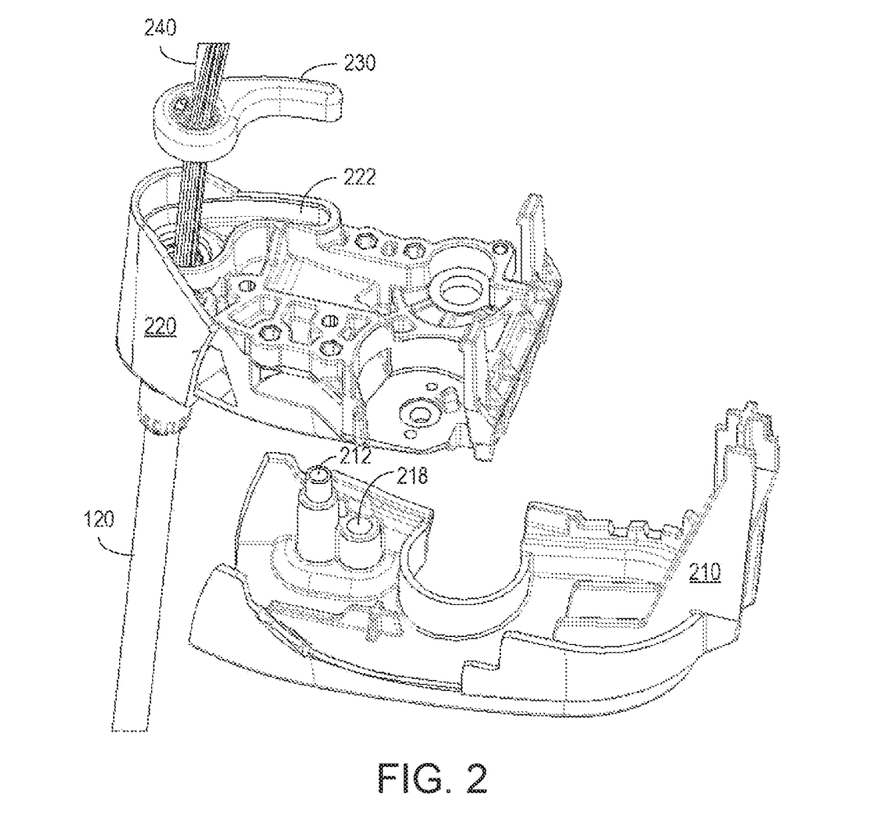
FIG. 2 shows an exploded view of a multi-piece chassis providing a fluid path through an instrument backend into an instrument shaft in a medical instrument in accordance with an example implementation.

FIG. 1A further shows how a housing of backend 130 may include an inlet 150 into which water or other cleaning fluid may be injected during cleaning of instrument 100. Inlet 150 may be sized and shaped to couple to standard cleaning equipment and in one specific implementation may include a Luer port fitting. The housing or chassis elements of backend 130 may route cleaning fluid from inlet 150 into a proximal end of instrument shaft 120. FIG. 2, for example, is an exploded view showing pieces 210 and 220 that fit together to form a portion of a housing or chassis for a medical instrument such as instrument 100. In some embodiments, piece 210 comprises a part or all of the housing and may be termed a housing piece. In some embodiments, piece 220 comprises a part or all of the chassis and may be termed a chassis piece. Piece 210 particularly includes a fluid channel from an inlet such as inlet 150 FIG. 1A to a hollow protrusion 212, and pieces 210 and 220 fit together so that the inlet is in fluid communication though hollow protrusion 212 with a fluid trough 222 in piece 220. In contrast to a separate tube as a fluid channel, structural pieces form the fluid channel.

Instrument shaft 120 is mounted in piece 220 so that a proximal end of instrument shaft 120 resides in trough 222. Instrument shaft 120 may also couple to a roll actuation mechanism (not shown), which may be mounted in an instrument backend as described in co-filed U.S. Pat. App. No. 62/362,340 (filed Jul. 14, 2016), entitled "GEARED ROLL DRIVE FOR MEDICAL INSTRUMENT." Drive elements 240, which may pass through fluid trough 222 and extend through instrument shaft 120 to a distal tool, may similarly have proximal ends connect to actuation mechanisms provided in an instrument backend as disclosed in co-filed U.S. Pat. App. No. 62/362,431 (filed Jul. 14, 2016), entitled "MULTI-CABLE MEDICAL INSTRUMENT." Drive elements 240 also pass through a cap 230 for trough 222. As described further, cap 230 may incorporate a guide for drive elements 240, and the cap and guide system may create a close fit to drive elements 240 to reduce of minimize loss of cleaning fluid through flush cap 230. Some cleaning fluid may leak through cap 230 into piece 210, but the housing comprising piece 210 is not required to be water tight, and any cleaning fluid that leaks around flush cap 230 may drain out through gaps, for example, between separate chassis or housing pieces, around input spindles 141 to 146 or through other openings 119 in backend 130 as shown in FIGS. 1A and 1B. An additional inlet 218 may allow secondary flushing of the backend 130 of any contaminants that may be back-washed from shaft 120 into the housing comprising piece 210 or introduced during handling of the instrument.

Figure 3A:
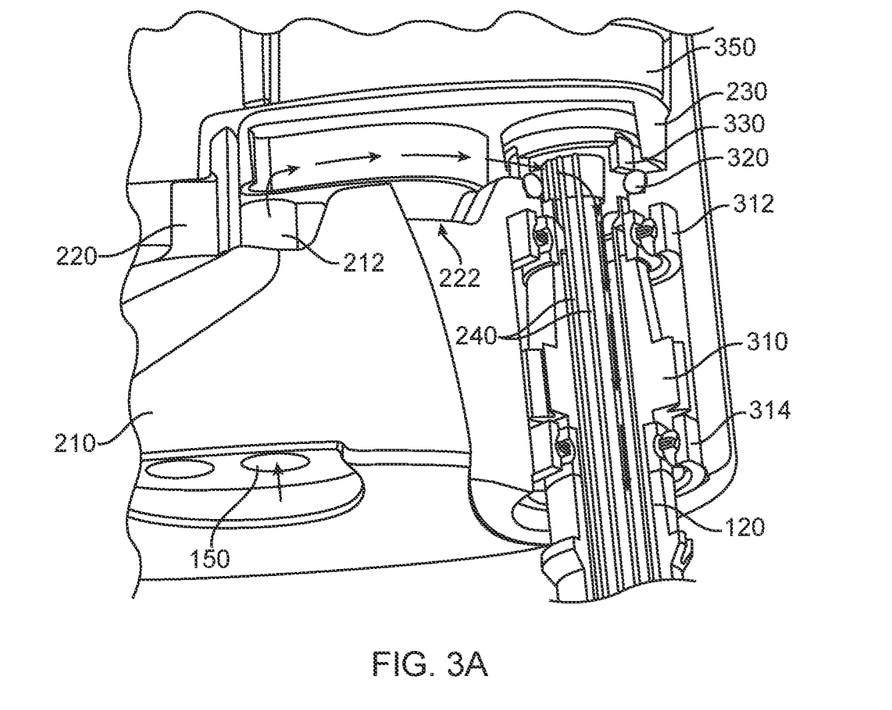
FIG. 3A shows a partial cutaway view of a flush path feeding a cleaning fluid through an instrument backend into an instrument shaft of a medical instrument in accordance with an example implementation.

FIG. 3A shows a partial cutaway view of a portion of the medical instrument of FIG. 2 when assembled. As shown, piece 210 includes inlet 150, which may include a female Luer port fitting and which terminates protrusion 212. Protrusion 212 may include a cone-shaped protrusion that fits snuggly into piece 220. Piece 210 may thus direct fluid into trough 222. Trough 222 in piece 220 in turn directs fluid for a short distance along the perimeter of the medical instrument to the location of the proximal end of instrument shaft 120.

Flush cap 230 fits in trough 222 to enclose a fluid channel from inlet 150 to the proximal end of instrument shaft 120. Flush cap 230 may have thin walls of a material that flex to allow a tight fit into piece 220. For example, flush cap 230 may be made of plastic. Cap 230 in one implementation is made of about 10 percent polytetrafluoroethylene (PTFE) to reduce friction against the driving elements, particularly grip drive rod 244, and the remaining 90 percent of cap 230 may be polyether imide (PEI), although other high temperature plastics would also be suitable. The thin walls of cap 230 may also press against the walls of trough 222 so that fluid pressure in the fluid channel has a tendency to tighten the seal of cap 230 against piece 220 and thereby resist or prevent fluid from leaking out around the edges of cap 230. A further chassis piece 350, which fits onto piece 220, may also capture flush cap 230 to keep fluid pressure or vibrations from pushing cap 230 out of place.

Figure 3B:
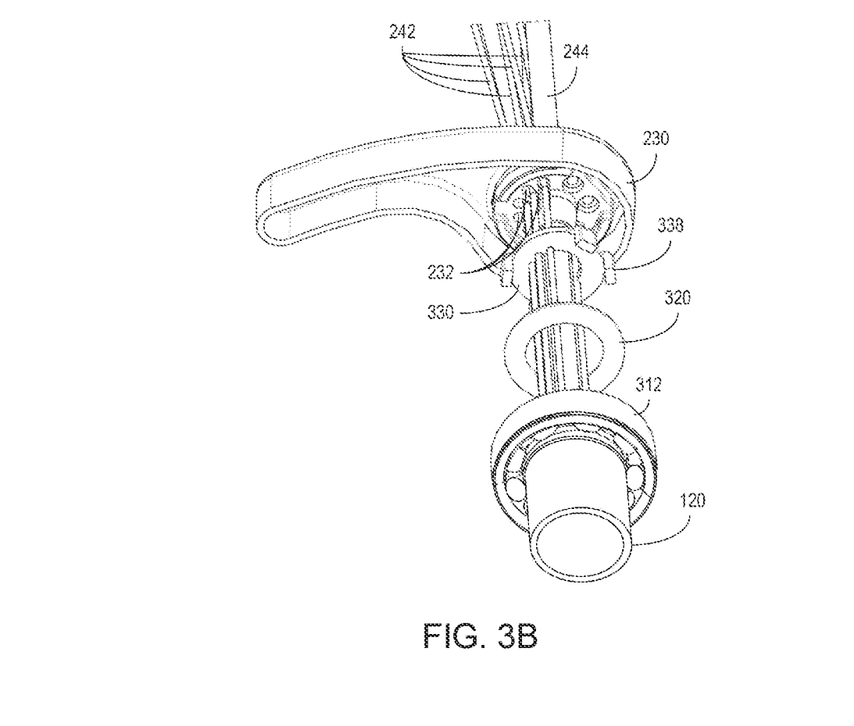
FIG. 3B shows an exploded view illustrating a flush cap and a cable guide through which drive elements may enter an instrument shaft of the medical instrument of FIG. 3A.

Holes 232 (also called "openings") in flush cap 230 as shown in FIG. 3B allow drive elements 240, such as drive cables 242 and a push-pull rod 244, to pass through cap 230. Drive elements 240 further extend through trough 222 and into instrument shaft 120. Cap 230 may be used with a cable guide 330 that supports the load that results from redirecting drive elements 240 from a path exiting instrument shaft 120 to a path towards drive mechanisms in the backend of the medical instrument. Cable guide 330 may be made of a resilient and durable material such as metal that will not be quickly eroded by the back-and-forth sliding of drive elements 240 against cable guide 330. For example, cable guide 330 may be made of hardened stainless steel and may support drive cables made of tungsten. In contrast, flush cap 230 may be made of a flexible material that may provide lower costs and a better seal against piece 220. An O-ring 320 may act as a spring to push cable guide 330 against flush cap 230.

A roll gear 310 as shown in FIG. 3A is coupled to instrument shaft 120 and may transmit rotation from a roll actuation mechanism to instrument shaft 120. The shape of the proximal end of roll gear 310, and the smallness of the gap between roll gear 310 and piece 220 may be used to direct most of the cleaning fluid from fluid trough 222 into instrument shaft 120 instead of out of the medical instrument through the gap to the outside of roll gear 310 and instrument shaft 120. Further, instrument shaft 120 may fit snugly inside roll gear 310 to similarly prevent leakage between instrument shaft 120 and roll gear 310. Proximal and distal roll bearings 312 and 314 support axial and radial loads on instrument shaft 120 and provide further sealing against leakage of cleaning fluid during a cleaning process. In particular, roll gear 310 may couple to instrument shaft 120 using gaps in roll gear 310 that may be mated to tabs on instrument shaft 120, and bearings 312 or 314 may cover such gaps so that the cleaning fluid stays inside instrument shaft 120.

Figure 4A:
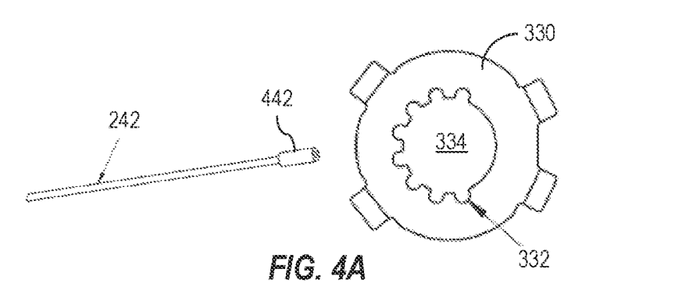
FIG. 4A shows a bottom view of an example implementation of a cable guide.
Figure 4B:
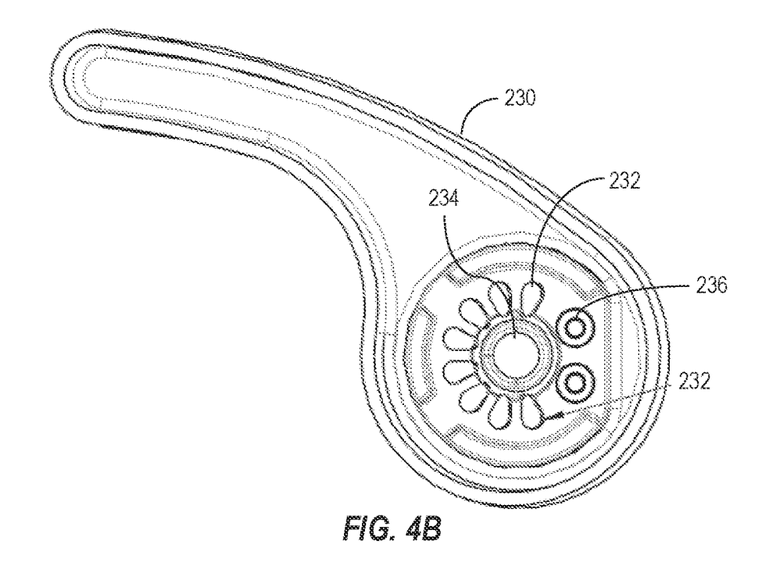
FIG. 4B shows a bottom view of an example implementation of a flush cap.
Figure 4C:
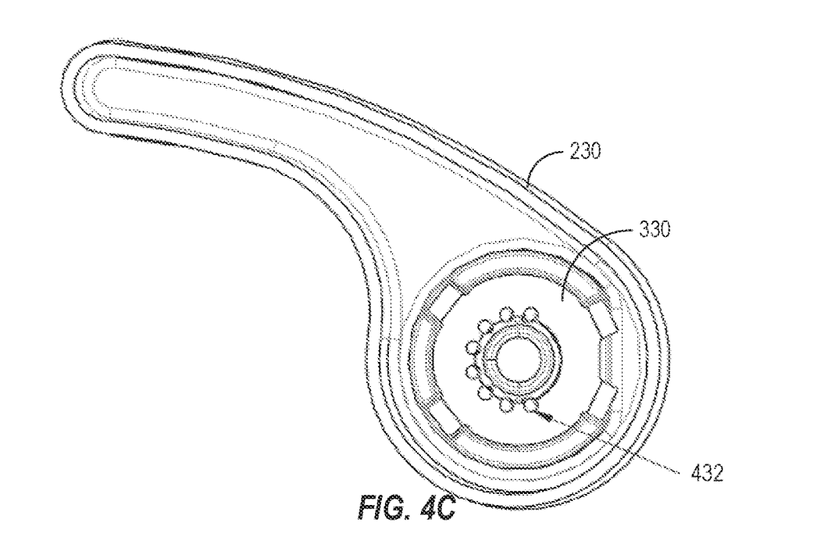
FIG. 4C shows a bottom view of the cable guide of FIG. 4A being pressed against the underside of the flush cap of FIG. 4B to form openings that seal around or closely fit drive cables.

FIGS. 3A and 3B show an implementation of a medical instrument in which push-pull rod 244 extends through center holes in flush cap 230 and cable guide 330, and drive cables 242 extend through separate holes in flush cap 230 and separate notches around the perimeter of the center hole in cable guide 330. In accordance with an aspect disclosed herein, flush cap 230 and cable guide 330 may be shaped to overlap and provide a close fit to drive cables 242. FIG. 4A, for example, shows a bottom view of one possible implementation of cable guide 330. In the implementation of FIG. 4A, cable guide 330 has U-shaped notches 332 around the perimeter of a central hole 334, and U-shaped notches 332 may be sized to closely fit respective cables 242. Further, each cable 242 may have an end 442 (which may comprise a crimp) with a diameter larger than U-shaped notches 332. Each end 442 may, for example, be used to connect a drive cable to an actuation mechanism, e.g., an input spindle. Cap 230 may have teardrop-shaped holes 232 as shown in FIG. 4B. In particular, an outer edge of each hole 232 may have a diameter large enough for threading of an end 442 of a cable 242 through the hole 232, and an inner edge of each hole 232 may be sized to snuggly fit a cable 242. When cable guide 330 is pushed up against flush cap 230, the overlap of holes 232 in cap 230 with corresponding U-shaped notches 332 creates through holes 432 that snuggly fit around cables 242 as shown in FIG. 4C. Through holes 432 may particularly be smaller than crimp or end 442 of a drive cable 242 but big enough to accommodate cable 242. The teardrop-shaped holes 232 in flush cap 230 may be oriented, shaped, and drafted or tapered so that the drive cables 242 touch only the metal of cable guide 330, so that flush cap 230 may be made of plastic or other relatively soft material and still will not wear away or decrease the amount of sealing during use. The central hole 234 in flush cap 230 may be similarly close fit to push-pull rod 244, so that the combination of cap 230 and cable guide 330 provides close fits around drive cables 242 and push pull rod 244, which inhibits leakage of cleaning fluid into the backend of the instrument. Push-pull rod 244 may follow a bend in instrument shaft 120, so that flush cap 230 may support a small radial load. Flush cap 230 may however be made of plastic as described above and may still support grip rod 244 with low friction, avoiding the problem of wear. After assembly, the close fit around drive cables 242 and drive rod 244 creates a path with high resistance to leakage and that directs most of the cleaning fluid down the instrument shaft instead of into the backend of the instrument. A complete seal is not necessary as long as a substantial portion of the water or other cleaning fluid is directed down the instrument shaft.

Assembly of the instrument using flush cap 230 and cable guide 330 can thread the larger end 442 of each drive cable 242 through central hole 334 in cable guide 330, before the cable 242 is seated in a U-shaped notch 332. Ends 442 may be similarly threaded through the larger out portions of holes 232 in cap 230, before cable guide 330 shifts cables 242 toward the smaller inner portions of holes 232 when cable guide 330 is pushed against cap 230. The two-piece cap structure thus enables pre-crimped cables to be passed through flush cap 230, which removes the need to crimp drive cables 242 on the assembly line after the drive cables 242 have been threaded through portions of a medical instrument being manufactured.

FIG. 4B also illustrates how cap 230 may include additional holes 236 for electrical lines, e.g., for a medical instrument that performs cauterization. As shown in FIG. 4C, cable guide 330 may omit holes for electrical lines when a medical instrument does not require an electrical connection to the distal tool, and cable guide 330 may seal holes 236 when cable guide is pressed against the underside of cap 230.

Returning to FIGS. 3A and 3B, O-ring 320 may be compressed between cable guide 330 and chassis piece 220 and therefore may push cable guide 330 up against the inside surface of flush cap 230. The bottom of cable guide 330 may include legs 338 that contact O-ring 320, so that gaps between legs 338 on cable guide 330 provide openings through which cleaning fluid passes to enter instrument shaft 120 during a flush or cleaning process. In an alternative implementation, O-ring 320 may be replaced with a spring or even a rigid surface/spacer that similarly pushes cable guide 330 against flush cap 230 and leaves openings for fluid flow into instrument shaft 120.

FIG. 4A as described above shows a cable guide 330 for a medical instrument that is a non-energized instrument, e.g., a medical instrument that does not require electrical lines extending through the instrument shaft. Accordingly, cable guide 330 of FIG. 4A has no holes for electrical wires and covers up holes 236 in flush cap 230 so water or other cleaning fluid does not get through holes 236 during a flush process.

Figure 5A:
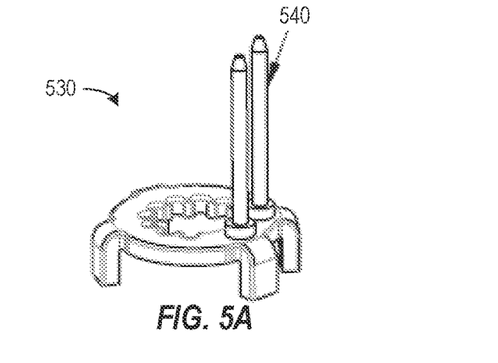
FIG. 5A illustrates an example implementation of a cable guide having connectors for lines used to electrically shield an instrument shaft.
Figure 5B:
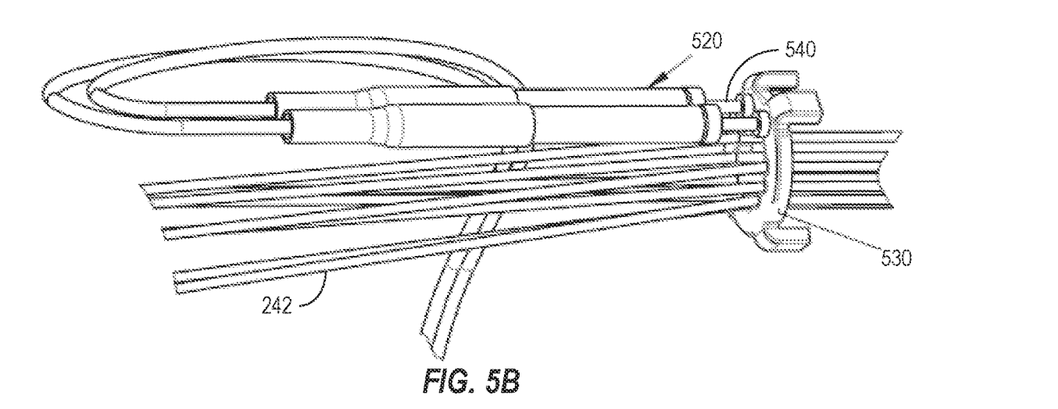
FIG. 5B shows the cable guide of FIG. 5A when the gable guide connected to electrical shielding lines guides drive elements of a medical instrument.

A medical instrument capable of monopolar cautery may electrically energize push-pull rod 244, so that push-pull rod 244 is used for both grip actuation and to conduct electrical power to jaws of the distal tool. A monopolar cautery instrument may, however, use electrical lines for electrical shielding of the instrument shaft. FIG. 5A, for example, shows a cable guide 530 having two pins 540 electrically coupled to cable guide 530. Pins 540 may be sized to fit through holes 236 and to close off holes 236 in flush cap 230 in order to block leakage of water or other cleaning fluid. As shown in FIG. 5B, shield wires 520 may be connected to pins 540 to ground metal cable guide 530, which when assembled in a medical instrument may be electrically connected to instrument shaft 120 and drive cables 242. Electrical shield wires 520 may alternatively be connected to cable guide 530 using other techniques, e.g., wires 520 may be crimped or soldered directly to cable guide 530 instead of using pins 540. Flush cap 230, which may be made of an electrically insulating plastic as described above, may include guide hole 234 for push-pull rod 244 so that push-pull rod 244 is electrically insulated from metal cable guide 530.

Figure 6A:
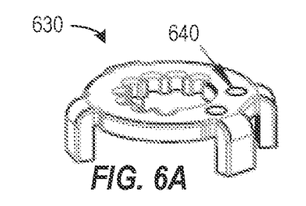
FIG. 6A illustrates an example implementation of a cable guide having openings for lines used to electrically energize a tool at the distal end of an instrument shaft.
Figure 6B:
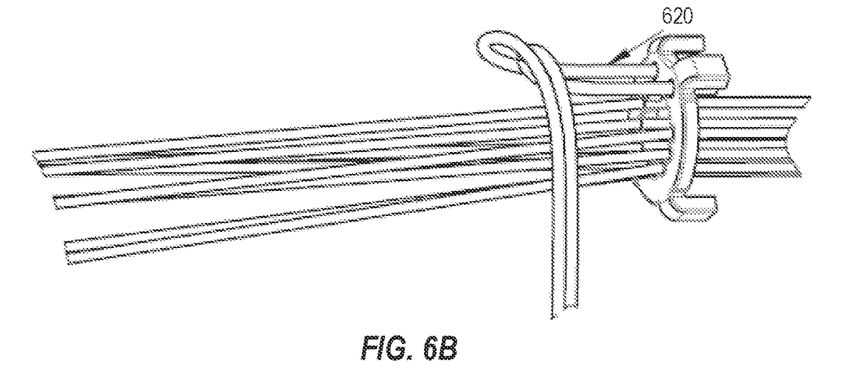
FIG. 6B shows the cable guide of FIG. 6A when the cable guide guides drive elements and electrical lines in a medical instrument.

A bipolar cautery instrument may employ electrical lines running through the instrument shaft alongside the drive cables. A cable guide 630 as shown in FIG. 6A may include two holes 640 for insulated wires or other electrically conductive lines 620 as shown in FIG. 6B to pass through en route to the distal tool. Insulated conductors 620 may substantially fill holes 640 in cable guide 630 or holes 236 in cap 230 so that water or other cleaning fluid will be directed away from cable guide 630 and mostly down the instrument shaft as in other implementations described above.

Some implementations of flush systems disclosed herein may provide several advantages over alternative flush systems. In particular, some flush systems disclosed herein do not require a flush tube extending through an instrument shaft and therefore may provide a more compact flush system that works in narrower instrument shafts and may provide a flush system that avoid problems that may arise when a flush tube becomes kinked. Further, implementations using a two-piece flush cap can complete a "seal" (not necessarily a perfect seal, but any leakage is at an acceptable amount) around each drive cable and still enable use of pre-crimped cables, which may simplify assembly of a medical instrument. Some implementations can direct cleaning fluid along a path of least resistance down the instrument shaft without requiring or using full seals on drive elements, which may avoid problems associated with seals that wear away quickly from the sawing action of the drive cables. Further, a flush path may be implemented with thin walled components mating together such that water or cleaning fluid pressure tends to increase the amount of sealing, which may improve reliability of cleaning a medical instrument.

Although particular implementations have been disclosed, these implementations are only examples and should not be taken as limitations. Various adaptations and combinations of features of the implementations disclosed are within the scope of the following claims.

What is claimed is:
1. A medical device, comprising:
a housing;
a shaft extending from the housing;
a drive element manipulation mechanism within the housing;
a drive element coupled to the drive element manipulation mechanism;
a cap comprising a cap opening; and
a guide comprising a guide opening;
wherein the guide opening overlaps with the cap opening to form a through hole smaller than the cap opening and smaller than the guide opening;
wherein the drive element extends from the drive element manipulation mechanism through the through hole and into the shaft; and wherein the through hole is sized to provide a close fit around the drive element to prevent a fluid from passing through the through hole.

2. The medical device of claim 1, wherein:
the medical device further comprises a second drive element;
the cap comprises a second cap opening;
the guide opening overlaps with the second cap opening to form a second through hole;
the second drive element extends from the drive element manipulation mechanism through the second through hole and into the shaft; and
the second through hole is sized to provide a close fit around the second drive element to prevent the fluid from passing through the second through hole.

3. The medical device of claim 1, wherein:
the drive element comprises a push-pull rod.

4. The medical device of claim 1, wherein:
the drive element comprises a drive cable.

5. The medical device of claim 4, wherein:
the medical device further comprises a crimp attached to the drive cable;
the crimp is sized to fit through the cap opening; and
the through hole is sized to prevent the crimp from passing through the through hole.

6. The medical device of claim 1, wherein:
the cap opening has a teardrop-shape.

7. The medical device of claim 1, wherein:
the guide opening comprises U-shaped notches.

8. The medical device of claim 1, wherein:
the medical device further comprises an O-ring; and
the O-ring is compressed between the guide and the housing.

9. The medical device of claim 1, wherein:
the medical device further comprises a fluid inlet and a trough in flow connection with the fluid inlet to receive the fluid;
the trough comprises sidewalls; and
the cap is inserted within the sidewalls of the trough.

10. The medical device of claim 9, wherein:
the cap comprises a flexible portion that seals against the sidewalls of the trough.

11. The medical device of claim 1, wherein:
the medical device further comprises an inlet for the fluid;
a path for the fluid is defined between the inlet for the fluid and the shaft; and
the drive element extends through the through hole into the path for the fluid.

12. The medical device of claim 11, wherein:
the shaft comprises a proximal end at the housing and a distal end opposite the proximal end;
the medical device further comprises a tool i-s-coupled to the distal end of the shaft; and
the tool comprises one or more vents through which the fluid flows after entering the shaft.

13. The medical device of claim 11, wherein:
the shaft comprises one or more vents through which the fluid flows after entering the shaft.

14. The medical device claim 1, wherein:
the guide comprises a metal material; and
the guide redirects a path of the drive element between the cap and the shaft.

15. A medical device, comprising:
a housing;
a shaft extending from the housing;
a drive element extending from the housing into the shaft;
a cap comprising a cap opening; and
a guide comprising a guide opening;
wherein the guide opening overlaps with the cap opening to form a through hole smaller than the cap opening and smaller than the guide opening;
wherein the drive element extends through the through hole; and
wherein the through hole is sized to provide a close fit around the drive element to prevent a fluid from passing through the through hole.

16. The medical device of claim 15, wherein the drive element comprises a drive cable or a push-pull rod.

17. The medical device claim 15, wherein the opening of the guide comprises U-shaped notches.

18. The medical device of claim 15, wherein the cap opening has a tear-drop shape.

19. The medical device claim 15, wherein:
the guide comprises a metal material; and
the guide redirects a path of the drive element between the cap and the shaft.

20. The medical device claim 15, wherein:
the medical device comprises an electrically conductive line;
the guide further comprises a cable hole; and
the electrically conductive line extends through the cable hole.

* * * * *

UNITED STATES PATENT AND TRADEMARK OFFICE
CERTIFICATE OF CORRECTION

PATENT NO. : 11,517,397 B2
APPLICATION NO. : 17/306498
DATED : December 6, 2022
INVENTOR(S) : Bram Gilbert Antoon Lambrecht, S. Christopher Anderson and Thomas G. Cooper It is certified that error appears in the above-identified patent and that said Letters Patent is hereby corrected as shown below:

In the Claims

Column 10, Line 6 (Claim 12): the phrase "a tool i-s-coupled to" should be – a tool coupled to –

Signed and Sealed this
Seventeenth Day of January, 2023

Katherine Kelly Vidal
*Director of the United States Patent and Trademark Office*